(12) United States Patent
Price et al.

(10) Patent No.: US 8,641,694 B2
(45) Date of Patent: Feb. 4, 2014

(54) FLUID CONTAINMENT POUCH

(75) Inventors: Delorse Louise Price, Columbus, MS (US); Richard H. Taylor, Columbus, MS (US)

(73) Assignee: Microtek Medical, Inc., St. Paul, MN (US)

( * ) Notice: Subject to any disclaimer, the term of this patent is extended or adjusted under 35 U.S.C. 154(b) by 630 days.

(21) Appl. No.: 12/825,949

(22) Filed: Jun. 29, 2010

(65) Prior Publication Data

US 2011/0319844 A1 Dec. 29, 2011

(51) Int. Cl.
*A61B 19/08* (2006.01)

(52) U.S. Cl.
USPC .......................... 604/355; 604/356; 128/849

(58) Field of Classification Search
USPC .......................... 128/849, 853, 855; 604/355
See application file for complete search history.

(56) References Cited

U.S. PATENT DOCUMENTS

| | | |
|---|---|---|
| 3,882,859 A | 5/1975 | Ericson |
| 4,081,306 A | 3/1978 | DePriest et al. |
| 4,169,472 A | 10/1979 | Morris |
| 4,559,937 A | 12/1985 | Vinson |
| 4,745,915 A | 5/1988 | Enright et al. |
| 4,869,271 A | 9/1989 | Idris |
| 4,890,628 A | 1/1990 | Jackson |
| 4,974,604 A | 12/1990 | Morris |
| 5,002,069 A | 3/1991 | Thompson et al. |
| 5,038,798 A | 8/1991 | Dowdy et al. |
| 5,161,544 A | 11/1992 | Morris |
| 5,209,243 A | 5/1993 | Glassman |
| RE34,512 E | 1/1994 | Dowdy et al. |
| 5,299,582 A | 4/1994 | Potts |
| 5,377,694 A | 1/1995 | Bark |
| 5,419,343 A | 5/1995 | Taylor |
| 5,494,050 A | 2/1996 | Reyes |
| 5,618,278 A | 4/1997 | Rothrum |
| 5,803,086 A | 9/1998 | Scholz et al. |
| 5,912,059 A | 6/1999 | Jones et al. |
| 6,032,670 A | 3/2000 | Miller |
| 6,213,124 B1 | 4/2001 | Butterworth |
| 6,314,958 B1 | 11/2001 | Harroll et al. |
| 7,588,034 B2 | 9/2009 | Mathis et al. |
| 7,594,512 B2 | 9/2009 | Reyes et al. |
| 2003/0196668 A1 | 10/2003 | Harrison |
| 2004/0006321 A1 | 1/2004 | Cheng |
| 2007/0207186 A1 | 9/2007 | Scanlon |
| 2008/0082059 A1 | 4/2008 | Fink |

FOREIGN PATENT DOCUMENTS

| | | |
|---|---|---|
| EP | 0 166 124 A2 | 1/1986 |
| GB | 1082743 | 9/1967 |

OTHER PUBLICATIONS

International Search Report of corresponding application PCT/IB2011/052827 mailed Apr. 4, 2012, 3 pages.

*Primary Examiner* — Susan Su
(74) *Attorney, Agent, or Firm* — IPLM Group, P.A.

(57) ABSTRACT

A fluid containment pouch is provided that includes a first layer of material having a first thermal characteristic and a second layer of material having a second thermal characteristic. The first layer of material is thermally compatible with a patient covering upon which it is to be thermally bonded. Thermal bonds between the fluid containment pouch and the patient covering form fluid containment channels that retain expelled body fluids during a patient's operation to help maintain a sterile operating environment.

12 Claims, 3 Drawing Sheets

FLUID CONTAINMENT POUCH

BACKGROUND

Operating rooms are maintained as a sterile environment to prevent contamination and the spreading of infections. One method of preventing the spread of contaminates is by covering patients during surgical procedures with patient drapes and patient incises and the like. Moreover, in maintaining a sterile environment, it is important to contain body fluids expelled from a patient during surgery.

For the reasons stated above and for other reasons stated below which will become apparent to those skilled in the art upon reading and understanding the present specification, there is a need in the art for an effective and efficient method of containing a patient's body fluids during an operation.

SUMMARY OF INVENTION

The above-mentioned problems of current systems are addressed by embodiments of the present invention and will be understood by reading and studying the following specification. The following summary is made by way of example and not by way of limitation. It is merely provided to aid the reader in understanding some of the aspects of the invention.

In one embodiment, a fluid containment pouch is provided. The fluid containment pouch includes first layer of material having a first thermal characteristic and a second layer of material having a second thermal characteristic. The first layer of material is thermally compatible with a patient covering. Thermal bonds between the fluid containment pouch and the patient covering form fluid containment channels that retain expelled body fluids during a patient's operation to help maintain a sterile operating environment.

BRIEF DESCRIPTION OF THE DRAWINGS

The present invention can be more easily understood and further advantages and uses thereof will be more readily apparent, when considered in view of the detailed description and the following figures in which.

In accordance with common practice, the various described features are not drawn to scale but are drawn to emphasize specific features relevant to the present invention. Reference characters denote like elements throughout Figures and text.

DETAILED DESCRIPTION

In the following detailed description, reference is made to the accompanying drawings, which form a part hereof, and in which is shown by way of illustration specific embodiments in which the inventions may be practiced. These embodiments are described in sufficient detail to enable those skilled in the art to practice the invention, and it is to be understood that other embodiments may be utilized and that changes may be made without departing from the spirit and scope of the present invention. The following detailed description is, therefore, not to be taken in a limiting sense, and the scope of the present invention is defined only by the claims and equivalents thereof.

Figure 1:
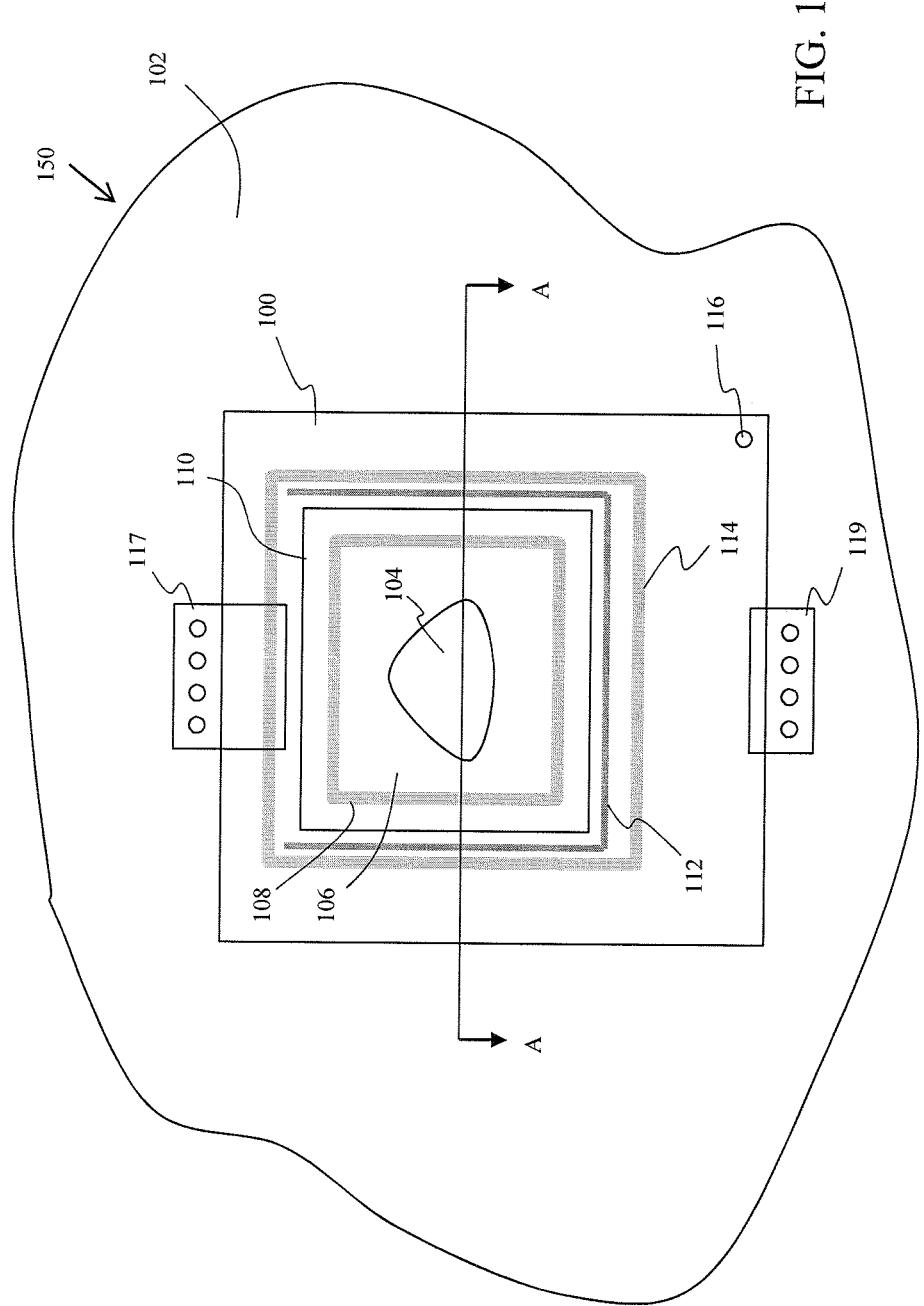
FIG. 1 is a top view of a fluid containment assembly of one embodiment of the present invention.

Embodiments of the present invention provide a fluid containment system designed to contain bodily fluids of a patient during an operation. In embodiments, a heat seal is used between a fluid containment pouch and a patient cover (substrate) to create a seal without seal channeling defects that can result in bodily fluids contaminating a sterile operative site. Examples, of fluid containment pouches include, but are not limited to, neuro pouches, C-section pouches, ophthalmic pouches, shoulder pouches, knee arthroscopy pouches and the like. Examples of patient covers, include but are not limited to, patient drapes, incises and the like. Referring to FIG. 1, a top view of a fluid containment assembly 150 of one embodiment is illustrated. The fluid containment assembly 150 includes a patient drape 102, a fluid pouch 100 and an incise 106 in this example embodiment. Attached to the patient drape 102 in this example are holding patches 117 and 119 used to hold and organize cords used during an operation. Also referring to the cross-sectional side view along line AA of FIG. 2, the fluid containment assembly 150 is further described. The incise 106 includes an adhesive layer 107 that is selectively applied to a patient prior to the start of an operation. The use of an incise 106 which typically is a clear polyurethane or polyethylene is common in C-section procedures. The incise 106 in this example embodiment has a central incise opening 104 where an incision can be made into a patient during a surgical procedure.

Figure 2:
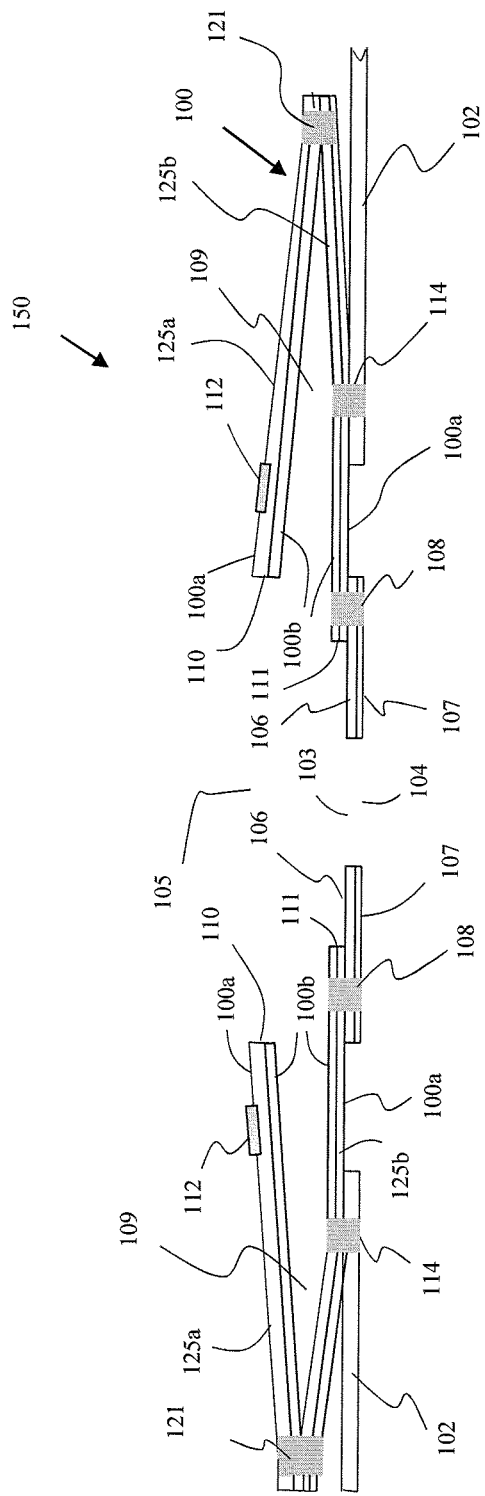
FIG. 2 is a cross-sectional side view of the fluid containment assembly across line AA of FIG. 1.

The fluid pouch 100 embodiment of FIGS. 1 and 2 has two layers 100a and 100b. The two layers 100a and 100b are made from different materials that have different melting characteristics. Examples of materials that make up the two layers 100a and 100b include, but are not limited to, polyurethane, polyethylene, polypropylene and polyester. For example, the first layer 100a could be made of polyurethane and the second layer 100b could be made of polyethylene. Another example is where the first layer 100a is made of polyethylene and the second layer 100b is made from polyurethane. It is preferred that the materials that make up the first and second layers 100a and 100b are transparent to allow for viewing fluid contained in fluid containment channels 109 formed by the pouch 100. In one embodiment, an example thickness range of the first and second layers 100a and 100b is approximately between 0.0006 and 0.0024 inches. Other thicknesses for the first and second layers 100a and 100b are contemplated in other embodiments. In one embodiment, the first and second layers 100a and 100b are formed with blow techniques known in the art of forming layered poly blend materials.

In one embodiment, the pouch 100 is formed by folding a first section of pouch material 125a over on a second section of pouch material 125b and then heat sealing 121 all non-connected edges. Since compatible material 100b (same melting point) are positioned next to each other on the edge seals 121, the edge seals 121 are formed free from seal channeling defects. The pouch 100 further has centrally aligned pouch openings 105 and 103 that are further aligned with incise opening 104. The pouch 100 is coupled to the incise 106 via heat seal 108. The heat seal 108 is accomplished by heating thermally compatible material layer 100a of the pouch with thermally compatible material of the incise 106 such as, but not limited to poly blend materials such as, polyethylene, polyurethane, polypropylene and the like. In this embodiment, the pouch 100 is further thermally coupled (heat sealed) to the patient drape 102 via thermal seals 114. Here again, thermally compatible material in layer 100a is heat sealed with thermally compatible material in the patient drape 102. For example, in one embodiment, layer 100a includes polypropylene and the drape 102 includes polypropylene. This seal 114 like the prior seals 121 and 108 discussed above, provide seals without seal channeling defects.

The pouch 100 of the fluid containment assembly 150 forms fluid containment channels 109 as briefly discussed above and as is shown in FIG. 2. Also included in the fluid containment assembly 150 are elongated manipulation members 112 that are coupled to the containment pouch 100 proximate opening 105. The elongated manipulation members 112 are generally bendable and in one embodiment contain at least one wire. The elongated manipulation members 112 help to position the sections 125a and 125b of the containment pouch 100 away from each other to allow fluid to pass into the formed fluid containment channels 109. Other methods of allowing fluid to pass into the containment channels 109 besides elongated manipulation members 112 are contemplated, such as but not limited to, the use of foam between the first section 125a and the second section 125b, other types of stiffeners and inflatable channels and the like. FIG. 1 further illustrates a port 116 that provides a passage into the fluid containment channels 109 to allow any fluid in the fluid containment channels 109 to be selectively drained via tube or the like into a container (not shown). During an operation, bodily fluids escaping from an incision will flow into the fluid containment channels 109 in the containment pouch 100. The fluid in the containment channels 109 can then be removed via port 116.

Figure 4A:
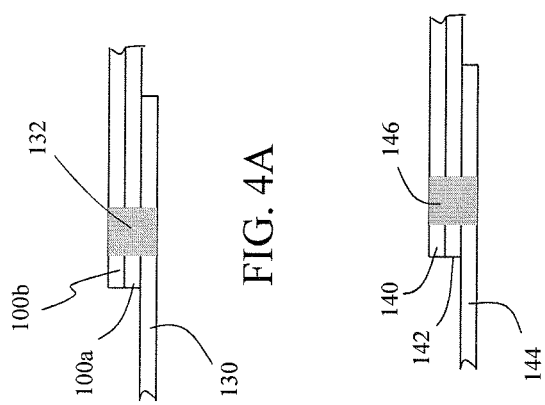
FIG. 4A is a side view of a portion of a fluid containment pouch coupled to a patient cover.
Figure 4B:
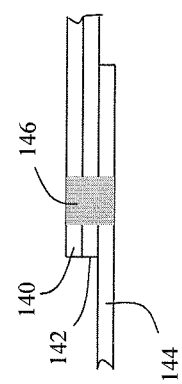
FIG. 4B is a side view of a portion of a fluid containment pouch of another embodiment coupled to a patient cover.
Figure 3:
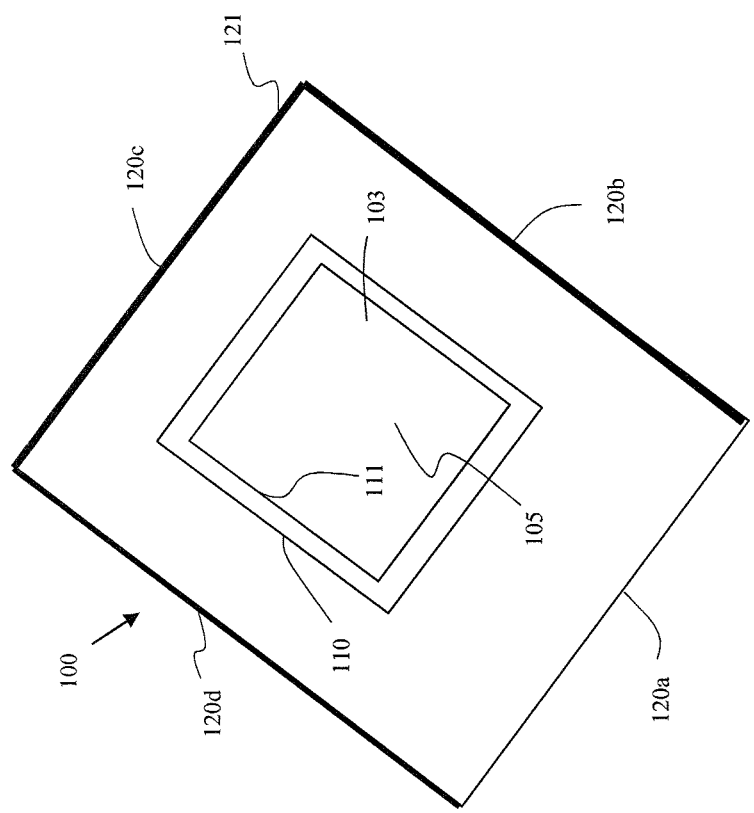
FIG. 3 is a top view of a fluid containment pouch of an embodiment of the present invention.

FIG. 3 illustrates a top view of the fluid containment pouch 100. As discussed above, in one embodiment, a section of material 125a is folded over on another section of material 125b in making the pouch 100. The folded edge 120a is illustrated in FIG. 3. The other edges 120b, 120c and 120d are heat sealed as discussed above. Also illustrated are aligned central pouch openings 103 and 105 and the respective inner edges 111 of the first section 125a of the material and inner edges 110 of the second section 125b of material that define the central openings 103 and 105. FIG. 4A illustrates a thermal bond 132 (heat seal) between two materials such as the two layers 100a and 100b of pouch 100 discussed above and a cover (substrate) 130 such as, but not limited to, an incise or patient drape. As discussed above, layer 100a will be thermally compatible with the substrate 130 to prevent seal channeling defects. In one example embodiment, the patient covering 130 is a polyester non-woven patient drape and the first layer 100a of the pouch 100 is a polyester layer. The second layer 100b may be in this example embodiment, a polyethylene layer. However, any type of thermally compatible layers as discussed above can be used. In FIG. 4B another embodiment is illustrated, in this embodiment although a first layer 140 (such as a layer of pouch material) is not thermally compatible with a second layer 144 (such as a patient covering) that it is to be coupled to, a layer of adhesive 142 is used so that when a thermal bond 146 is created, a seal is formed without seal channeling defects. Hence, in this embodiment an adhesive, such as but not limited to, transfer adhesive or double sided tape can be used when the materials to be bonded are generally not thermally compatible. Heat seals made by this method prevent seal channeling defects from forming later due to relief of interfacial stress even in generally non-thermally compatible bonded materials.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

The invention claimed is:

1. A fluid containment pouch comprising:
a first layer of material having a first thermal characteristic, the first layer of material being thermally compatible with a patient covering;
a second layer of material having a second thermal characteristic that is different than the first thermal characteristic of the first layer, the second layer of material positioned adjacent the first layer of material to form a pouch material, at least one first section of the pouch material positioned over a second section of pouch material to form at least one channel having at least one outer edge, the second layer of material being heat sealed together proximate the at least one outer edge;
the first section of the pouch material having a first opening; and
the second section of the pouch material having a second opening, the second opening being at least in part aligned with the first opening, wherein the first opening and the second opening provide access through the fluid containment pouch to a patient during a surgical procedure.

2. The fluid containment pouch of claim 1, wherein the patient covering is at least one of an incise and a patient drape.

3. The fluid containment pouch of claim 1, wherein the at least one first section of pouch material is folded over the second section of pouch material to form the at least one channel.

4. The fluid containment pouch of claim 1, wherein the first and second openings are centrally located within the respective first and second section.

5. The fluid containment pouch of claim 1, further comprising:
a port formed in one of the first and second sections configured and arranged to provide a passage for fluid contained in the at least one channel to be removed from the fluid containment pouch.

6. A fluid containment assembly comprising:
a patient drape configured and arranged to cover at least a portion of a patient; and
a fluid containment pouch made from a pouch material having a first layer of a first material and a second layer of a second material, the first material having a first melting point and the second material having a second melting point, the second melting point of the second material being different than the first melting point of the first material, the first layer of the fluid containment pouch thermally coupled to the patient drape, at least one first section of the pouch material positioned over a second section of pouch material to form at least one channel having at least one outer edge, the second material of the first section and the second material of the second section being heat sealed together proximate the at least one outer edge.

7. The fluid containment assembly of claim 6, wherein the at least one first section is folded over the second section of pouch material to form the at least one channel.

8. The fluid containment assembly of claim 6, wherein the first and second material layers are one of polyurethane, polyethylene, polypropylene and polyester.

9. The fluid containment assembly of claim 6, further comprising an incise.

10. The fluid containment assembly of claim 6, wherein the fluid containment pouch is coupled around a cover opening in the patient drape.

11. The fluid containment pouch assembly of claim 10, wherein the fluid containment pouch includes a pouch opening aligned with the cover opening.

12. The fluid containment pouch assembly of claim 6, wherein the fluid containment pouch and the patient drape form fluid channels to hold a patient's bodily fluids.

* * * * *